United States Patent [19]
Decker et al.

[11] Patent Number: 5,607,405
[45] Date of Patent: Mar. 4, 1997

[54] SURGICAL INSERTION DEVICE AND METHOD

[76] Inventors: Rand A. Decker, 3609 E. Crestmount Cir., Salt Lake City, Utah 84121; Ludwig F. Kroner, 2143 Carson St., Rock Springs, Wyo. 82901

[21] Appl. No.: 241,042

[22] Filed: May 9, 1994

Related U.S. Application Data

[63] Continuation of Ser. No. 885,459, May 19, 1992, abandoned.

[51] Int. Cl.$^6$ ............................. A61M 5/00; A61M 25/00
[52] U.S. Cl. ........................... 604/264; 604/280; 606/167; 606/185
[58] Field of Search ................................... 604/164, 166, 604/167, 171, 264, 280, 272–274; 606/167, 184, 185

[56] References Cited

U.S. PATENT DOCUMENTS 3,714,945  2/1973  Stanley ................................. 604/164
4,461,280  7/1984  Baumgartner ........................ 604/164

Primary Examiner—John G. Weiss
Assistant Examiner—Dennis Ruhl
Attorney, Agent, or Firm—Trask, Britt & Rossa

[57] ABSTRACT

Apparatus for surgical insertion of medical apparatus such as a drain into a patient is disclosed. The apparatus includes a trocar with a pierceable sheath covering the forward point, a handle removably affixed to the rear end, and a notch formed on the trocar just behind the point. The notch facilitates gripping of the trocar with a tool during removal of the trocar from the patient's body. Optionally, a kit including the insertion apparatus is further provided with a suitable such tool. In a preferred embodiment, the tool is configured as a protective case handle which can be affixed by means of the engagement structure to enclose the trocar point. The case handle both aids in removal of the trocar, and protects personnel handling the trocar during the procedure and during subsequent disposal of the trocar.

8 Claims, 6 Drawing Sheets

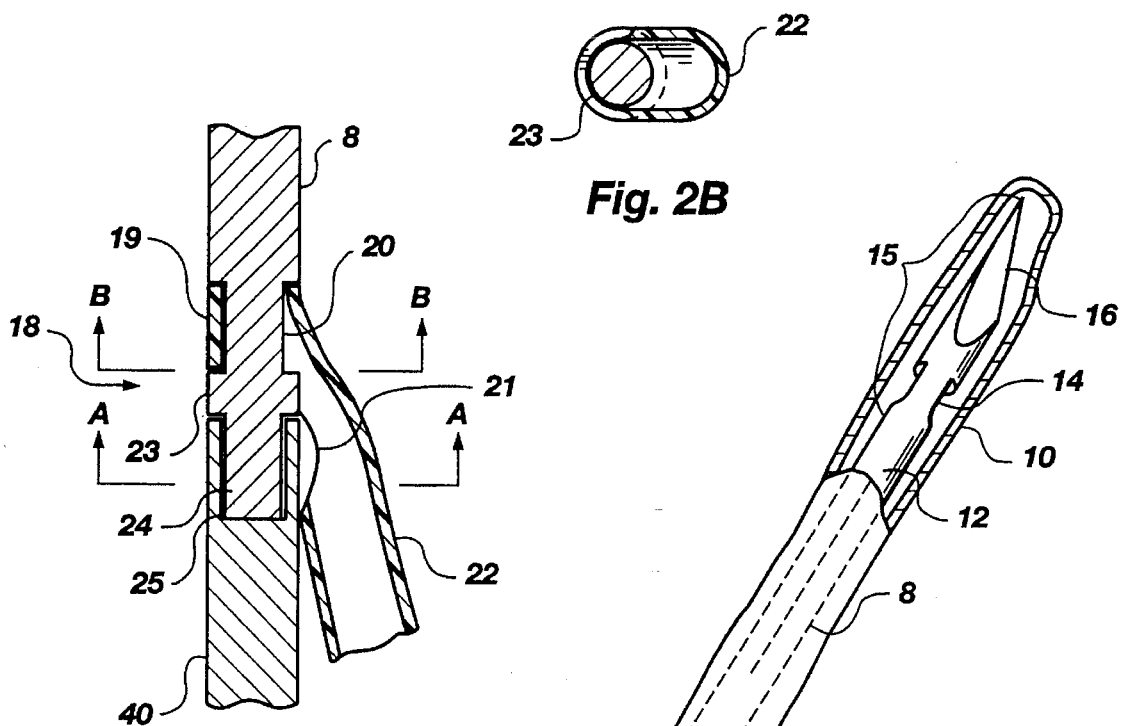
Fig. 2B
Fig. 2
Fig. 2A
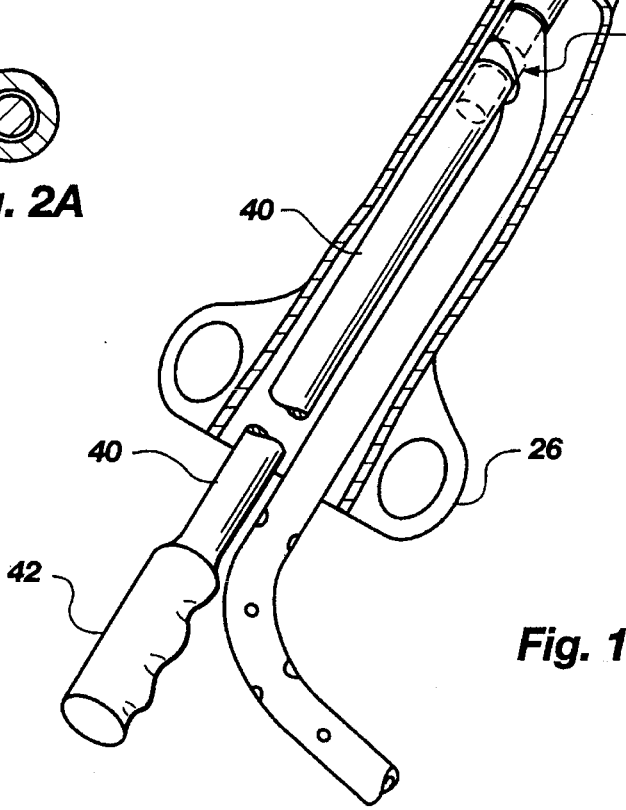
Fig. 1

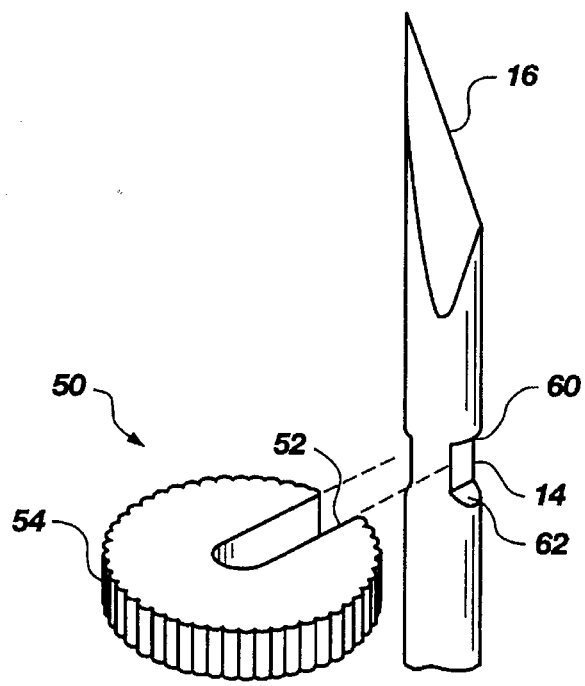
Fig. 3
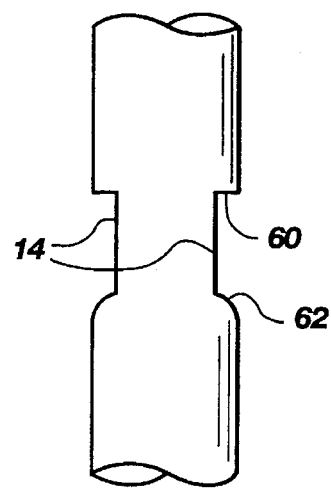
Fig. 4
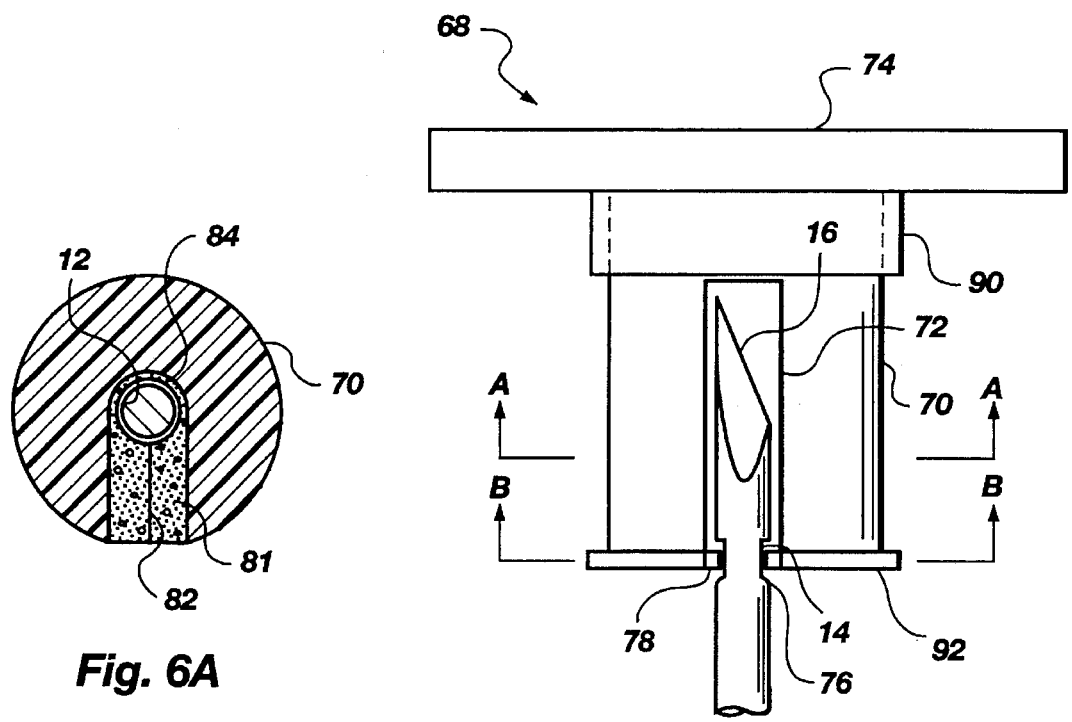
Fig. 6A
Fig. 5

SURGICAL INSERTION DEVICE AND METHOD

RELATED APPLICATIONS

This application is a continuation of Ser. No. 07/885,459 filed May 19, 1992, now abandoned.

BACKGROUND OF THE INVENTION

1. Field

This invention relates to surgical instruments and more particularly to devices for inserting drains and the like.

2. State of the Art

The technique of arthroscopic surgery has been developed for use particularly with knees and shoulders, to minimize the incision and disruption of the joint during extensive repairs to various parts of the joint including ligaments and cartilage. During these procedures, as in many other surgical procedures, it is often necessary to insert a tube into the affected body part to drain fluids which would otherwise accumulate. It is desirable to perform this procedure in a manner causing the least possible damage to other nearby tissues and internal structures. In arthroscopic knee surgery, for example, it is highly desirable to avoid damaging the articular cartilage.

The standard trocar used for insertion of a drain in arthroscopic procedures is an elongated member with a circular cross-section having a bend or angle along its length and a sharp forward point for piercing sacs or cavities in which fluid collects. The drain itself is usually a piece of flexible tubing having one end hooked to a device for aspirating the interior of the tubing. The other end of the tubing may be connected to the rear end of the trocar, by fitting snugly over a threading or by other removable means.

In use, a standard trocar with drain tubing attached is inserted into a surgical incision. The surgeon maneuvers the trocar using a wrench-like tool to grip the rear end of the trocar, until the tip is adjacent a boundary membrane of the sac whose drainage is desired. Force is then exerted to urge the trocar point to pierce the sac, and to push it until the trocar pierces the skin to exit the limb approximately on the opposite side from the incision. The surgeon then grips the trocar tip with the same or similar wrench-like tool, pulls the trocar out of the exit cut, and detaches the tubing from the rear end of the trocar, usually by pulling the tubing in the rearward direction. The end of the tubing is then pulled back into the limb until it is positioned within the sac.

The above-described trocar and method of placement of a drain during arthroscopic procedures have several disadvantages. First, the exposed tip of the trocar can cause injury to the tissues inside the joint as it is inserted through the arthroscopic incision and is maneuvered to the sac. Standard trocars have an angled shank designed to follow a curved path within a hip joint, whereas with knee or shoulder joints it is usually desirable to pass the trocar in a straight line, to facilitate pushing the trocar to pierce the sac and to exit the limb. Manipulation of the trocar is performed using a wrench or pliers-like tool to grip the trocar's proximal end, which is prone to slippage since the trocar end typically has a circular cross-section. Slippage of the grip on the trocar is a particular problem when force is exerted to push the trocar through otherwise intact body tissue. The standard trocar is also relatively short in length, further increasing the difficulty of grasping and maneuvering with the tool.

Moreover, removing the trocar as it exits the joint is also problematic. The forward end of the trocar must be gripped with a tool to pull it free from the exit wound. However, the trocar presents a smooth exterior on which it is difficult to maintain a grip when the necessary force is applied to pull on the trocar. The gripping tool is thus prone to slip free, or the trocar may fly loose from the tool as it is pulled from the exit wound, and cause injury to nearby personnel. Also, the surgeon's hand can slip and be punctured by the trocar point. Such punctures carry the risk of transmission of the HIV (AIDS) virus, hepatitis virus, or other serious infectious microorganisms. Thus, it is especially desirable to avoid even minor punctures.

Accordingly, a need remains for a surgical trocar for insertion of drains which provides improved ease of manipulation and protects the patient from unnecessary damage to tissues adjacent the incision.

Additionally, there is a further need for a trocar having means to facilitate its removal from a patient's exit wound. It is particularly desirable to have such trocar removal means which will prevent accidental punctures to medical personnel.

SUMMARY OF THE INVENTION

The invention is a surgical insertion device useful to insert drains, probes, or other medical apparatus into a patient. The surgical insertion device includes a trocar to which the item (such as a drain or probe) to be inserted may be attached, a removable sheath covering the sharp forward tip of the trocar, and a handle removably affixed to the rear end of the trocar. The handle provides a hand-grip for maneuvering the trocar point-first into a surgical incision in a patient's body part. The sheath covers the trocar point until the point is positioned adjacent tissue whose penetration is required to provide an exit wound for the trocar. The trocar point can then be exposed by piercing and/or retracting the sheath, and further manipulated via the handle to form the exit wound.

A preferred embodiment includes engagement structure on the trocar tip just behind the sharp point. Such engagement structure provides a secure grip for a tool when the point has exited the patient, thereby facilitating detachment of the handle and pulling of the trocar from the exit wound. The engagement structure may take the form of a pair of flat-bottomed notches. A kit including the insertion apparatus is desirably provided with a gripping tool useful for gripping the notch(es) on the trocar.

In a highly preferred embodiment, the gripping tool is configured as a safety guard which can be affixed by means of the notches to encase the sharp trocar point. The tool may have handle means associated thereto to aid in pulling the trocar from the exit wound.

BRIEF DESCRIPTION OF THE DRAWINGS

In the figures, which depict what is presently regarded as the best mode of carrying out the invention, like numbers represent like elements, and FIG. 1 is an overall view of the surgical inserter showing the sheath and handle of the invention, with drain tubing to be inserted attached thereto;

FIG. 2 is a detail cross-section view of the attachment of the handle to the trocar taken along line 2—2 of FIG. 1;

FIG. 2A is a cross-section detail view taken along section line A—A of FIG. 2;

FIG. 2B is a detail cross-section view of the association of the tubing with the proximal end of the handle taken along section line B—B of FIG. 2;

FIG. 3 is a detail view of a trocar and a gripping tool according to the invention;

FIG. 4 is a side detail view of the trocar of FIG. 3;

FIG. 5 is a side view of a trocar encased in the T-grip trocar cover handle of the invention;

FIG. 6A is a cross-section view of the trocar encased in a case tool, taken along line A—A of FIG. 5;

DETAILED DESCRIPTION OF THE INVENTION

Figure 6B:
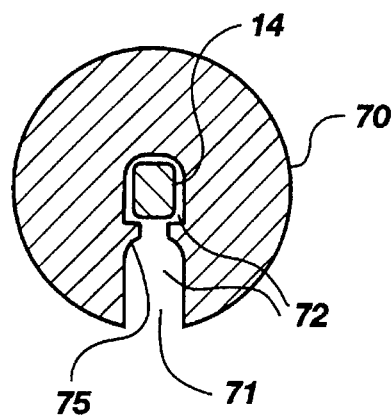
FIG. 6B is a cross-section view of the case tool taken along line B—B in FIG. 5.

The invention comprises an apparatus and method for inserting a drain, probes, or other medical apparatus into the interior of a patient's body in conjunction with a surgical procedure. The surgical insertion apparatus includes trocar means having a distal tip terminating in a sharp forward point, and a pierceable sheath disposed to cover the trocar tip during its passage to the region of the patient's body which is to be pierced. The trocar means also includes a shank and a proximal end configured for detachable association of the medical apparatus to be inserted, and, in preferred embodiments, for detachable association of a handle.

FIG. 1 shows an embodiment of a surgical inserter according to the invention. Trocar 12 is encased in a sheath 10 shown in partial cutaway and having tabs 26. Trocar 12 includes a shank 8, a distal tip 12 with sharp point 16 and engagement structure 14 formed behind the point 16, and a proximal end 18. Engagement structure 14 (a pair of flat-bottomed notches) can be firmly gripped by a tool for pulling trocar 12 from the exit wound. In an embodiment preferred for use in arthroscopic procedures involving knees, shank 8 of the trocar is straight rather than angled, and is substantially longer than a standard trocar.

Sheath 10 as shown in FIG. 1 has a tip end which is closed to cover trocar point 16, and finger loop tabs 26 extending exterior to the entry incision when the inserter is in use. Desirably, sheath 10 also has perforations near the tip end to facilitate its piercing by trocar point 16. Alternatively, the tip of sheath 10 could be open-ended and extend somewhat beyond trocar point 16 to afford protection of the point. Any tab means such as strips or a widened open end of sheath 10 could be used in place of finger loop tabs 26.

A handle 40 is removably attached to the proximal trocar end 18 by means of corresponding structures on trocar end 18 and handle 40. Handle 40 is of length sufficient to have the grip portion 42 exterior to the entry incision during use of the surgical inserter. Also shown is a drain tubing 22 comprising a flexible plastic tubing formed with perforations in the section to be disposed within the body region whose drainage is desired. Trocar portion 18 is configured to have drain tubing 22 detachably mountable thereto.

FIG. 2 shows the proximal trocar portion 18 of the embodiment of FIG. 1 in detail. A circumferential groove 20 is formed on the trocar for detachably mounting drain tubing 22 (or a probe or other apparatus which may be disposed within a tubing, tied to a string, or otherwise attached to the trocar) thereto. A tang 24 forming the end of trocar portion 18 is configured to engage with a frictional bushing 25 disposed within handle 40 for detachably securing the trocar thereto. Tang 24 and bushing 25 are shown in cross-section in FIG. 2A.

Drain tubing 22 has a port 21 in the side wall of the tubing near one end. Port 21 provides access for attachment of handle 40 to the trocar proximal portion 18. Tubing end 19 adjacent to port 21 is configured to fit snugly but removably into groove 20 of the trocar to hold drain tube 22 to the trocar during insertion. The major portion of drain tube 22 is thus displaced sideward from the longitudinal axis of the trocar, as seen in FIG. 2B. A hub 23 which may be similar in width to the trocar shank keeps tubing end 19 from slipping off until it is cut or otherwise deliberately detached by the surgeon.

Sheath 10 is configured to envelop handle 40 and drain tubing 22 in the segments which enter the patient's body part during use of the surgical inserter. Since sheath 10 enters the body, it is imperative that it be sterile at the time of use.

Figures 7, 8:
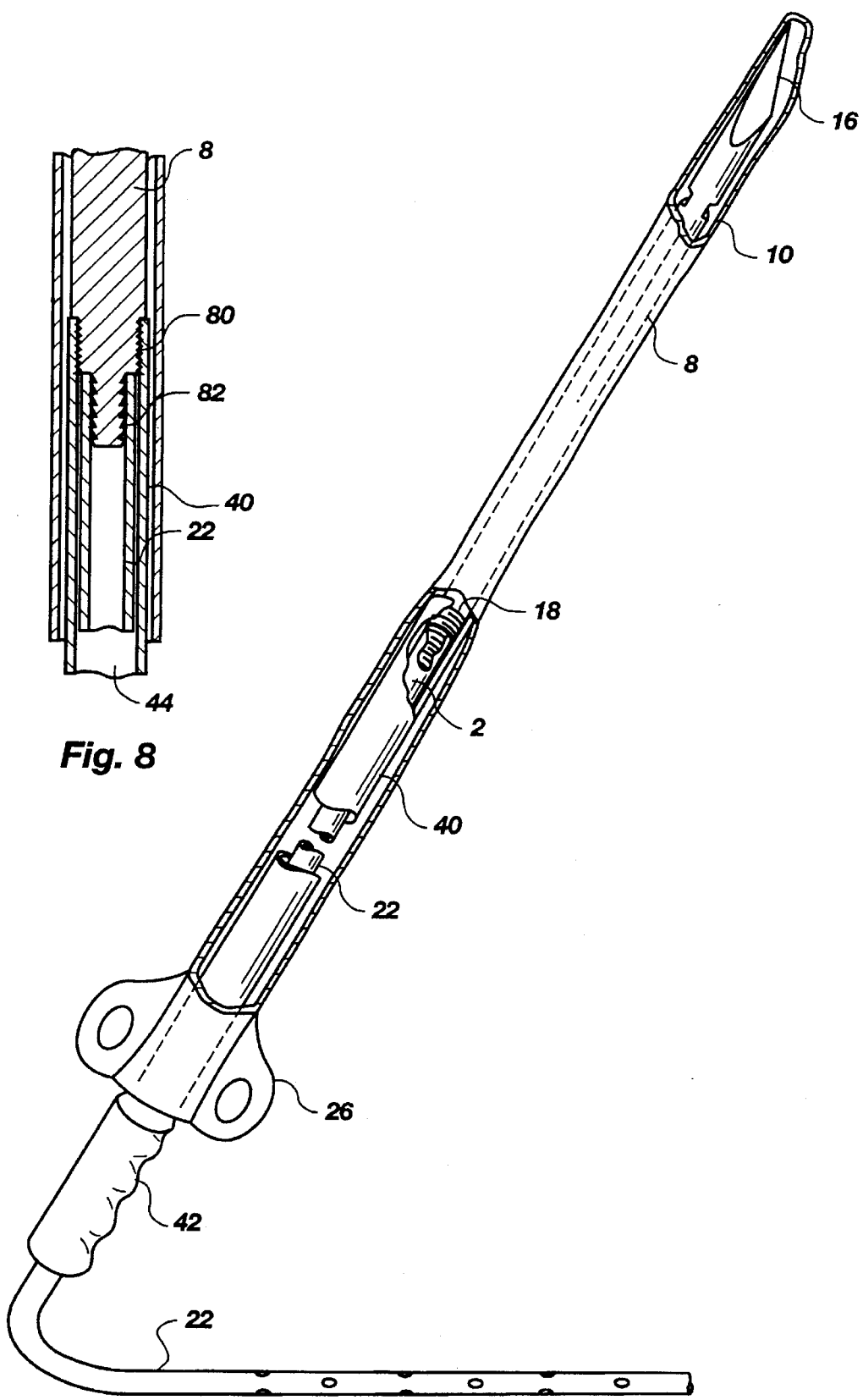
FIG. 7 is an overall view of a second embodiment of the surgical inserter having an alternate configuration for attachment of the handle means and disposition of a drain tubing.
FIG. 8 is a cross-section detail of the embodiment of FIG. 7 taken along line 8—8.

In an alternate embodiment shown in FIGS. 7 & 8, proximal trocar end 18 has a ribbed or notched segment 82 over which drain tube 22 fits grippingly and detachably. Trocar end 18 also has a threaded segment 80 which can be screwed to handle 40 by means of corresponding threads thereon. In this embodiment, handle 40 has a longitudinal interior channel 44 open at the grip end 42 through which drain tubing 22 passes.

FIG. 3 shows a detail of an embodiment having the trocar tip with the engagement structure and a tool for engaging the engagement structure to grip the trocar. FIG. 4 shows the trocar dual notch engagement structure in greater detail with the edge 60 proximal to the point 16 having a flat surface cut substantially at right angles to the longitudinal axis of the trocar. The edge 60 so configured aids the tool in pulling the trocar outward from the exit wound. In a preferred embodiment, edge 62 which is distal to the trocar point 16 is smooth and sloping. Such a sloping edge enables the engagement structure 14 to slide smoothly as the trocar is advanced point-first through a patient's body part, without catching on tissues or internal structures.

One embodiment of a tool is that shown in FIG. 3. Tool 50 has a deep rabbet 52 configured to snugly receive the dual notch engagement structure 14, and the outer rim surface 54 is desirably ribbed or textured to facilitate gripping by a user when force is exerted to twist the trocar and to pull it from the exit wound. Alternatively, the tool could be provided with a handle for the user to grip.

In a preferred embodiment, the tool is configured as a safety guard or cap for placement over the trocar point to shield medical personnel from punctures during removal of the trocar from the patient. The guard can be affixed to the trocar by means of the dual notch engagement structure 14 behind the point. In a highly preferred embodiment, the guard is provided with handle means for gripping by the medical practitioner. The tool/guard is placed over the trocar point after its emergence from the exit wound, affixed to the trocar by means of the engagement structure, and used to pull the trocar from the wound. The tool/guard so used prevents puncture injuries to the surgeon and other nearby personnel. The trocar can be disposed of with the point 16 still enclosed in the case, thus also preventing inadvertent puncture injuries to persons handling the medical wastes.

FIG. 5 illustrates an embodiment of such a tool/guard 68 with a trocar point encased therein. A guard cap 70 has a channel 72 with an open channel side 80 extending longitudinally up the case and a lower opening 76 at the bottom of the case. The embodiment of FIG. 5 further includes grip means here shown as a bar-like structure 74 associated with the upper end of the cap. Channel 72 comprises means for seating the trocar point and engagement structure within guard cap 70.

Channel 72 is desirably provided with means for retaining trocar point 16 within channel 72. Such retaining means may take any of several forms, or a combination thereof. In the embodiment of FIG. 5, cap 70 includes an inner flange 78 disposed on the interior surface of channel 72 for preventing the trocar from slipping out of the lower opening 76 of channel 72. Flange 78 is configured to fit around the engagement structure 14 of the trocar as shown in FIG. 6A. In FIG. 5, flange 78 is shown with the flange edges forming the lower opening 76 of channel 72. However, in principle flange means 78 can be disposed in any position in the vertical direction along the interior surface of channel 72, providing enough space above the flange for the trocar point to fit therein.

Retaining means are also desirable to prevent the trocar point 16 from slipping out of the vertical open side of channel 72. Such retaining means may be a ring-like structure 90 slidably mounted over the exterior of the case (FIG. 5). Ring 90 is movable between a first position in which the open side of channel 72 is entirely exposed (as shown in FIG. 5) and a second position in which the open side is at least partially occluded (see FIG. 10). Desirably, guard cap 70 has an outer flange 92 on the exterior surface for retaining ring 90 in association with the case.

As illustrated in FIG. 6A, the retaining means may further include a compressible foam or foam-like packing 81 having a slit 82 leading to a cylindrical channel 84 oriented parallel to channel 72. When the trocar point is seated in channel 84, packing 81 helps to prevent its dislodgement through the open side of channel 72. Foam packing 81 may be used with or without ring 90. Still another embodiment is depicted in FIG. 6B, wherein flanges 78 of FIG. 5 are replaced by modified flanges 75, made of a semirigid material. Modified flanges 75 are flexible enough to permit the trocar to be inserted into channel 72 through the side opening 71, but also stiff enough to significantly impede dislodgement of the trocar back out of the opening 71 and to function similarly to flanges 78 in FIG. 5, which prevent the sharp point 16 from being pulled back through the bottom of the channel.

Figure 6C:
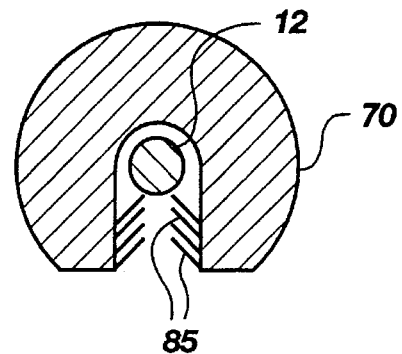
FIG. 6C is a cross-section view of an alternate embodiment of the case tool taken along line A—A of FIG. 5.
Figure 6D:
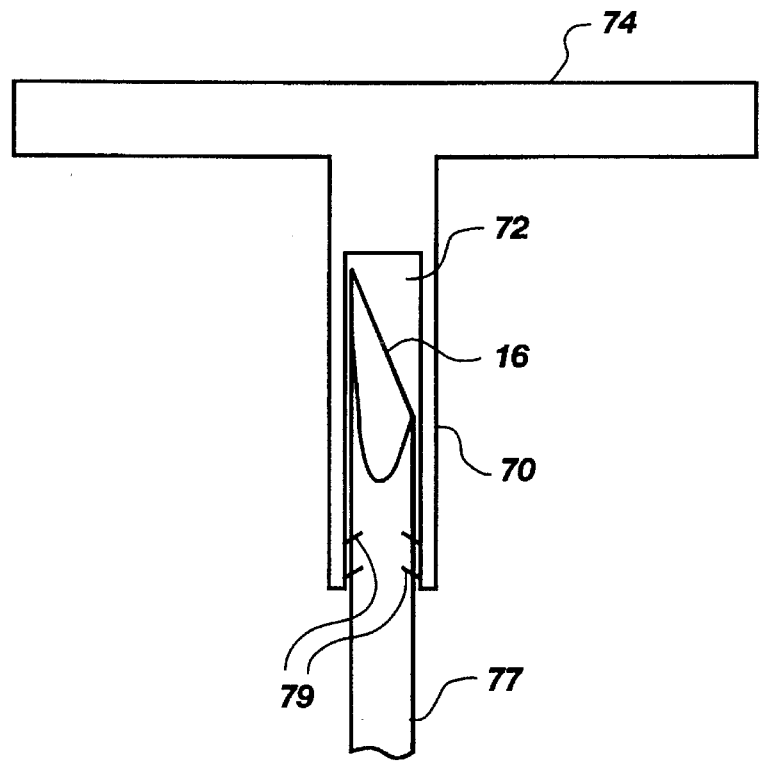
FIG. 6D is a side view of a standard (un-notched) trocar encased in an alternate embodiment of a T-grip trocar cover handle.

An alternate embodiment of a retaining means is shown in FIG. 6C in the form of claw-like structures 85 angled inward from the sides of channel 72. FIG. 6D depicts still another embodiment of a retaining means, which may be used with a conventional trocar 77 lacking the notch 14 of the trocar of FIGS. 3–5 herein. The cap shown in FIG. 6D has two pairs of sharp ratchets 79 located on the inside of the cavity and angled towards the closed end of the cavity. These ratchets are of sufficient length and sharpness to prevent trocar 77, once inserted in the channel 72, from being pulled to a significant extent out of the interior of the cap.

The invention may be effectively embodied as a kit for inserting a drain insertion or other medical apparatus, for example a probe, a fiber optic viewing apparatus, etc. Such a kit would include a trocar having one or more of the following previously described features: a pierceable trocar sheath; a detachable rear handle; and/or a gripping engagement structure on the trocar. Desirably, such a kit will include a tool for gripping the engagement structure on the trocar. Optionally, the kit may include drain tubing or other medical apparatus to be inserted. Additionally, for maximum convenience and usefulness the contents of the kit would be packaged with the components already sterilized and partially or totally assembled in the manner shown generally in FIGS. 1 and 7. Sterility of the kit may be maintained by sealing the components in a plastic envelope or other airtight packaging.

Figure 9:
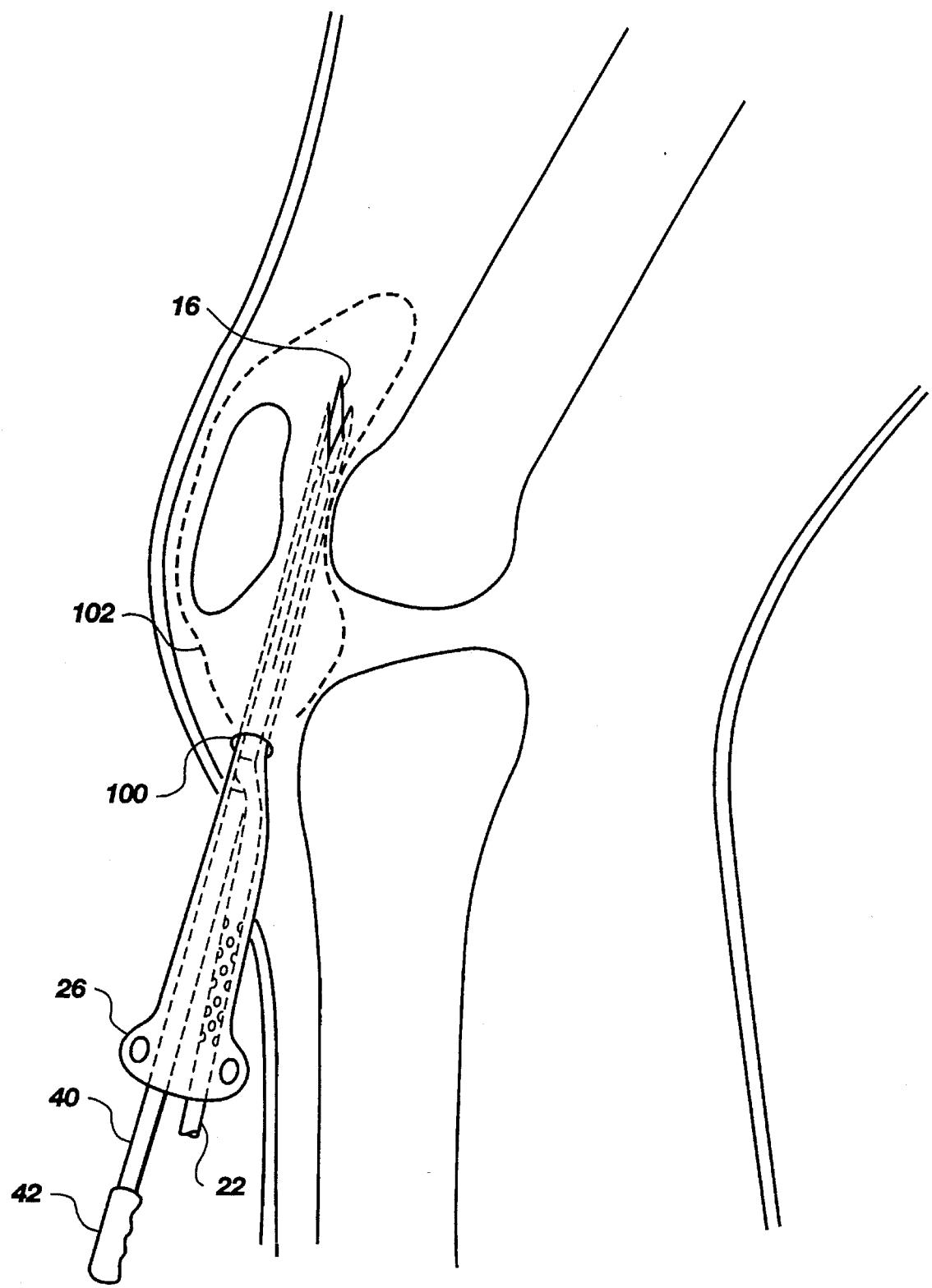
FIG. 9 illustrates a step of unsheathing the trocar point during the insertion of a drain.
Figure 10:
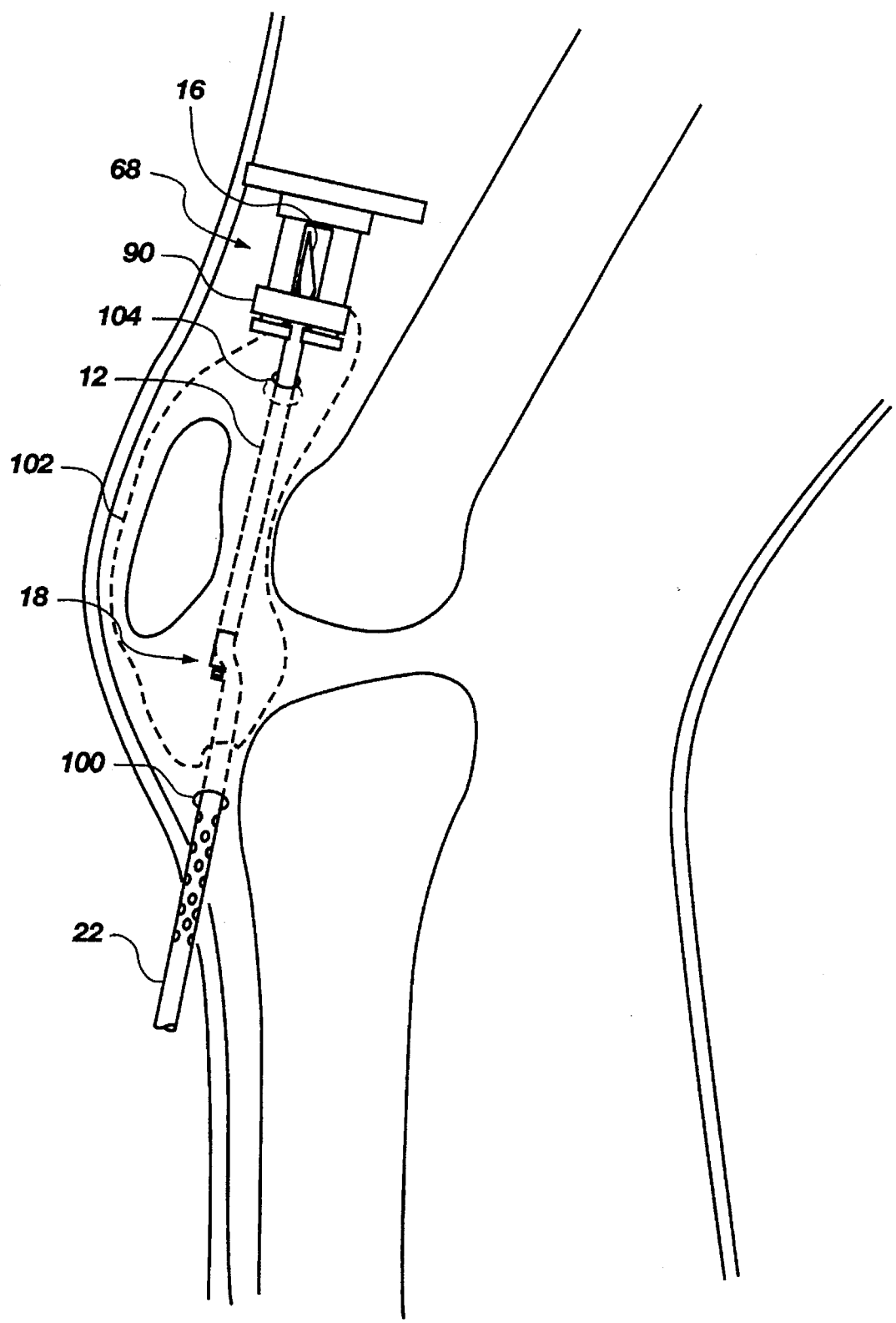
FIG. 10 illustrates a step of using the case tool of FIG. 5 for removal of the trocar and detachment of the drain tubing.

The invention further embraces a method of using a surgical insertion apparatus comprising some or all of the elements outlined previously herein. FIGS. 9 and 10 illustrate two stages of such a method as it would be performed with a surgical inserter assembled to drain tubing as shown in FIGS. 1 or 7.

Trocar 12 enveloped in the sheath 10 is inserted tip first into a surgical incision 100. The surgeon grips handle 40 to manipulate the trocar into the body cavity 102 in which the drain (and/or other medical apparatus) is to be inserted. Upon positioning the sheathed trocar tip adjacent the opposing intact wall of the cavity, the surgeon uses tabs 26 to pull sheath 10 onto trocar point 16, thereby piercing the sheath and exposing trocar point 16 as shown in FIG. 9. Note that at this stage, the exit wound 104 of FIG. 10 has not yet been created. Sheath 10 may now be pulled back out the entry incision by means of tabs 26, or it may be left partially in place to protect tubing 22 from contact with non-sterile materials.

Next, the exposed trocar point 16 is urged to pierce the cavity wall, to pass through the hole created by the trocar point, and eventually to exit the patient's body through an exit wound 104 also created by the trocar point at a location distal to the entry incision 100. Still grasping handle 40 affixed to the trocar, the surgeon uses a tool to grip engagement structure 14 on trocar 12. In FIG. 10, the tool is shown as being the case tool 68 of FIG. 5, but the tool 50 of FIG. 3, or other means of gripping the flattened notches of engagement structure 14, may be used. While the trocar is gripped at its engagement structure 14, handle 40 is detached from the trocar proximal end 18, as is shown in FIG. 10.

Trocar 12 may then be pulled outward from exit wound 104 by means of the tool until the distal end 23 of drain 22 is positioned as desired with respect to the cavity to be drained. Drain 22 is then detached from proximal end 18 of the trocar. In one embodiment of the method, trocar 12 is pulled until proximal end 18 has emerged substantially entirely from exit wound 104, and drain 22 is cut to detach it from the trocar. The cut end of drain 22 is then pulled back into the exit wound and positioned near or within the cavity. Drain 22 is then left in place for as long as desired. If case tool 68 is employed to remove trocar 12, the trocar may be discarded while still encased therein.

While the method is described primarily with reference to insertion of a drain, it will be recognized that other types of medical apparatus, for example the previously mentioned probes or fiber optic viewing devices, can be inserted by similar means, adapted as necessary and obvious to those skilled in the art.

Desirably, drain tubing 22 is provided with a calibrated portion having marks distributed at intervals along its length. These marks are for aiding in the positioning of the perforated segment within the patient's body part. In use, when the practitioner believes that the perforated segment is positioned as desired within the patient's body part, she or he notes which particular mark is nearest exterior to the entry incision. When the trocar point is pulled from the exit wound, the distal end of the tubing (that attached to the trocar) is in turn pulled further into the patient's body part. The practitioner then re-positions the perforated segment by pulling on the proximal end of the tubing (the end extending from the entrance incision) until the noted mark is in the desired position.

The surgical inserter used in manner described hereinabove provides much greater ease of manipulation and substantially protects the patient from unnecessary tissue injury during initial insertion. Additionally, the risk of accidental punctures to medical personnel is greatly reduced by the improved gripping of the trocar attained by means of the engagement structure, and by the use of the protective guard/tool.

A trocar according to the invention is typically formed of stainless steel, similar to prior art trocars. Desirably, the trocar is somewhat longer than typical prior art trocars, perhaps 5" to 7" long. The trocar further has diametrical dimensions compatible with standard sizes of drain tubing. A typical example has an interior diameter of $3/16$", but other diameters are possible Groove 20 in the embodiment of FIG. 1, or the end portion having notch-like ribs 82 in the embodiment of FIG. 8, should be of diameter allowing such drain tubing to fit snugly but removably thereover. The trocar shank should be of diameter about $1/16$" to $1/8$" greater than groove 20 or ribs 82. Engagement means 14 formed as a dual notch near the trocar point, and tang 24 and groove 20 of the embodiment shown in FIG. 1, are formed by milling of the trocar. A more expensive construction is shown in FIGS. 7 & 8, where trocar proximal portion 18 has threads 80 and notch-like ribs 82.

In gripping tool 50 of FIG. 3, the body of the tool could be made of plastic cut from a solid cylinder formed in a mold, with notch 52 milled therein. Case handle 68, shown in FIGS. 5 & 6, is desirably made by injection molding of plastic to form the body 70 and handle 74 as an integral unit. Cavity 72 and opening 76 are then milled into the body.

The invented surgical insertion apparatus and method have a number of advantages. First, sheath 10 covering trocar point 16 during insertion prevents trauma to tissues through which the trocar passes, while allowing the point 16 to be exposed when needed to form an exit wound. Handle 40 attached to the rear end of the trocar makes maneuvering of the trocar by the user much easier. Handle 40 also makes it easy to unsheathe the trocar point by holding trocar 12 still while pulling down on sheath tabs 26. Engagement structure 14 near the trocar point, and the tool which grips trocar 12 by the engagement structure, greatly facilitate the pulling of the trocar from the exit wound. The tool having a safety guard configured to encase trocar point 16 substantially eliminates the risk to the user and others of incurring puncture wounds from the trocar during its removal and disposal.

While the invention is described in terms of specific embodiments, it is recognized that a range of equivalents in the way of sheath structures, attachment structures for the handle, engagement structures for the tool, etc., are possible. The claims recite those aspects regarded as essential to the invention.

What is claimed is:

1. A method of using a surgical insertion kit having a trocar with a sharp point covered by a protective sheath, engagement structure formed on the trocar near the point, a drain detachably associable to the trocar, a trocar handle detachably affixed to the trocar, and a tool affixable to the engagement structure for a user to thereby grip the trocar, comprising the steps of:

inserting the sheathed trocar with the drain detachably associated thereto into a surgical entrance incision in a patient;

using the trocar handle to maneuver the trocar point to a desired position within the patient;

unsheathing the trocar point;

urging the trocar point to exit the patient's body part through an exit wound created by the unsheathed trocar point;

gripping the trocar with the tool;

detaching the trocar handle from the trocar;

pulling the trocar from the exit wound;

detaching the drain from the trocar; and repositioning the drain in the desired location within the patient's body part.

2. A surgical insertion kit for emplacing a drain tube into an interior region of a patient's body part during a surgical procedure, comprising:

a trocar having a distal portion terminating in a sharp point, a proximal portion adapted for removably attaching a drain tube, and a shank connecting said proximal and distal portions;

handle means removably attached to said proximal portion for gripping by a user, said handle means having cross-sectional dimensions greater than said trocar;

wherein said trocar is structured to be passed through said body part absent said handle means;

a pierceable sheath configured to enclose said sharp point, made of a material pierceable by said sharp point, and having an open end portion of length sufficient to extend beyond said proximal portion of said trocar; and a safety cap configured for mounting on said distal end of said trocar to encase said sharp point, and wherein said trocar further has mounting means formed on said shank adjacent said sharp point for mechanically affixing said safety cap thereto.

3. A surgical insertion kit for emplacing a drain tube into an interior region of a patient's body part during a surgical procedure, comprising:

a trocar having a distal portion terminating in a sharp point, a proximal portion adapted for removably attaching a drain tube, and a shank connecting said proximal and distal portions;

handle means removably attached to said proximal portion for gripping by a user, said handle means having cross-sectional dimensions greater than said trocar;

wherein said trocar is structured to be passed through said body part absent said handle means;

a pierceable sheath configured to enclose said sharp point, made of a material pierceable by said sharp point, and having an open end portion of length sufficient to extend beyond said proximal portion of said trocar; and wherein said trocar further has a first indent region located on said proximal portion, and further including a flexible tubing comprising a sidewall and first and second ends, said first end being open, and said sidewall having an aperture near said first end and a series of smaller perforations near said second end, and wherein said first open end and said aperture are dimensioned to fit snugly but removably in said first indent region.

4. A trocar kit providing safe removal of a trocar point used in an arthroscopic procedure in which a trocar inserted into a patient's body part through an entrance slit is pulled by the trocar point from an exit point, comprising:

a trocar having a distal portion terminating in a sharp point, a proximal portion having a drain attaching means formed thereon for detachably attaching a drain tube, a shank connecting said proximal and distal portions, engagement structure formed on said distal portion rearward and adjacent said sharp point; and a safety tool comprising a chamber sized to encase said sharp point, engagement means disposed on said chamber for securely engaging said engagement structure, and grip means for gripping by a user; said kit further including a drain tube constructed with perforations for draining a patient's wound, and wherein said proximal portion of said trocar is formed with attachment means for attaching said drain tube.

5. The trocar kit of claim 4, further including a pierceable sheath made of a material pierceable by said sharp point, of length greater than said trocar, and having a closed end and an open end, said closed end formed to enclose said sharp point.

6. The trocar kit of claim 4, further including handle means removably attached to said proximal portion of said trocar for grasping by a user, said handle means having cross-sectional dimension greater than said trocar, and wherein said trocar is structured to be passed through said body part absent said handle means and removed by engagement with said safety tool.

7. The trocar kit of claim 4, wherein said safety tool is constructed to be disposable.

8. The trocar kit of claim 4, wherein said trocar further has an indent region located on said proximal portion, and wherein said drain tube has a sidewall and first and second ends, said first end being open and said sidewall having an aperture near said first end, and said first end and said aperture are dimensioned to fit snugly but removably in said indent region.

* * * * *